United States Patent [19]

Shaw

[11] 4,380,569
[45] Apr. 19, 1983

[54] LIGHTWEIGHT PREFORMED STABLE GEL STRUCTURES AND METHOD OF FORMING

[75] Inventor: Robert E. Shaw, Waco, Tex.

[73] Assignee: Spenco Medical Corporation, Waco, Tex.

[21] Appl. No.: 289,223

[22] Filed: Aug. 3, 1981

[51] Int. Cl.³ .............................................. B32B 5/16
[52] U.S. Cl. ........................................ 428/283; 3/36; 128/479; 264/41; 264/DIG. 6; 428/280; 428/281; 428/282; 428/284; 428/325; 428/402; 428/405; 428/406; 428/447
[58] Field of Search ............. 264/41, DIG. 6; 428/71, 428/76, 241, 325, 405, 406, 447, 304.4, 313.3, 313.9, 312.6, 68, 317.9, 283, 284, 280, 281, 282; 128/479, 481; 3/36

[56] References Cited

U.S. PATENT DOCUMENTS

| | | | |
|---|---|---|---|
| 2,482,297 | 9/1949 | Silverman | 2/267 |
| 2,542,619 | 2/1951 | Bernhardt | 2/267 |
| 2,543,499 | 2/1951 | Kausch | 2/267 |
| 2,636,182 | 4/1953 | Freedman | 2/267 |
| 2,698,436 | 1/1955 | Bernhardt | 2/267 |
| 2,727,278 | 12/1955 | Thompson | 18/59 |
| 2,842,775 | 7/1958 | Pangman | 3/36 |
| 2,867,818 | 1/1959 | Creamer | 3/36 |
| 2,897,821 | 8/1959 | Lerner | 128/479 |
| 3,067,431 | 12/1962 | Kausch | 3/36 |
| 3,099,839 | 8/1963 | Kestor | 3/36 |
| 3,189,921 | 6/1965 | Pangman | 3/36 |
| 3,190,292 | 6/1965 | Barnes | 128/479 |
| 3,278,947 | 10/1966 | Silverman | 3/36 |
| 3,293,663 | 12/1966 | Cronin | 3/36 |
| 3,304,558 | 2/1967 | Mann | 3/36 |
| 3,308,491 | 3/1967 | Spence | 5/348 |
| 3,366,975 | 2/1968 | Pangman | 3/36 |
| 3,401,407 | 9/1968 | Pittman | 3/36 |
| 3,416,160 | 12/1968 | Arion | 3/36 |
| 3,494,365 | 2/1970 | Beak | 128/479 |
| 3,514,792 | 6/1970 | Freedman | 3/36 |
| 3,548,420 | 12/1970 | Spence | 3/20 |
| 3,559,214 | 2/1971 | Pangman | 3/36 |
| 3,600,718 | 8/1971 | Boone | 3/36 |
| 3,641,592 | 2/1972 | Bleyker | 3/36 |
| 3,663,973 | 5/1972 | Spence | 5/348 |
| 3,665,520 | 5/1972 | Perras et al. | 3/36 |
| 3,681,787 | 8/1972 | Perras | 3/36 |
| 3,852,832 | 12/1974 | McGhan et al. | 3/36 |
| 3,896,506 | 7/1975 | Hankin et al. | 3/36 |
| 4,019,209 | 4/1977 | Spence | 3/36 |
| 4,024,876 | 5/1977 | Penrock | 128/472 |
| 4,134,848 | 1/1979 | Adecoff et al. | 428/313.9 |
| 4,152,384 | 5/1979 | Apps | 264/41 |
| 4,256,803 | 3/1981 | Savey et al. | 428/313.7 |

FOREIGN PATENT DOCUMENTS 2094826 1/1972 France .

*Primary Examiner*—James J. Bell
*Attorney, Agent, or Firm*—Richards, Harris & Medlock

[57] ABSTRACT

A lightweight preformed stable gel composition formed by admixing a gel mixture of silicon gels and catalyst with glass microspheres, pouring the mixture into a mold and reacting the mixture. The resulting composition is a preformed stable silicon gel with glass microspheres dispersed throughout.

35 Claims, 5 Drawing Figures

LIGHTWEIGHT PREFORMED STABLE GEL STRUCTURES AND METHOD OF FORMING

TECHNICAL FIELD

This invention relates to the formation of lightweight preformed stable gels and products manufactured therefrom, and more particularly to a stable gel structure in which void spaces have been provided by glass microspheres.

BACKGROUND ART

In one aspect the present invention relates to an improved method for making stable gel structures which results in increased production rates, lower costs, and reduced weight. In another aspect, the invention relates to a lightweight preformed stable gel composition which comprises a stable gel throughout which glass microspheres have been dispersed. In still a further aspect, the invention relates to structures made from the lightweight gel.

Gels have been heretofore used for a variety of purposes which utilize the characteristic behavior of gels to distribute a force applied thereto radially in all directions. For example, gels have been used in the construction of cushions to distribute weight uniformly and to absorb shock. U.S. Pat. Nos. 3,308,491 issued to Spence on Mar. 14, 1967 and entitled "Cushion Structure" and 3,548,420 issued to Spence on Dec. 22, 1970 and entitled "Cushion Structure" disclose cushions that provide uniform distribution of a patient's weight to prevent pressure necrosis when confined for long periods in a bed or wheelchair or as padding in artificial limbs. Cushions of this type may also be employed as floormats to relieve fatigue for workers who must stand for long periods such as on an assembly line.

Preformed stable gel has also been employed in the manufacture of prosthetic devices to simulate the feel and movement of the human body, and, in particular, as disclosed by U.S. Pat. No. 4,019,209 issued to Spence on Apr. 26, 1977 and entitled "Artificial Breast Form and Method of Forming".

The present invention includes preparing a reaction mixture which will form on reaction a self-contained stable gel in which void spaces have been provided by dispersion of glass microspheres throughout. The reaction mixture containing glass microspheres is poured into a mold of any desired shape. The resulting preformed stable gel structure which is sticky may be covered with a variety of coverings dependent on the function of the structure is intended to perform. Preferably the covering selected does not substantially constrain the gel, for example, a latex rubber or an elastic fabric.

A disadvantage of structures utilizing previous gel compositions is that the resulting structures were relatively heavy. The formed stable gel with glass microspheres dispersed throughout made in accordance with the present invention is lighter in weight and more economical to manufacture than gels formed entirely of gel material. While lighter and more economical to manufacture, the lightweight gel composition of the present invention retains the capability of absorbing relatively large shearing forces without fracturing, remains stable over relatively wide temperature range, is nonfriable and hypoallergenic. The novel features believed characteristic of the invention are set forth in the appended claims.

BRIEF DESCRIPTION OF THE DRAWINGS

A more complete understanding of the invention and its advantages will be apparent from the Detailed Description taken in conjunction with the accompanying drawings in which.

DETAILED DESCRIPTION

Figure 1:
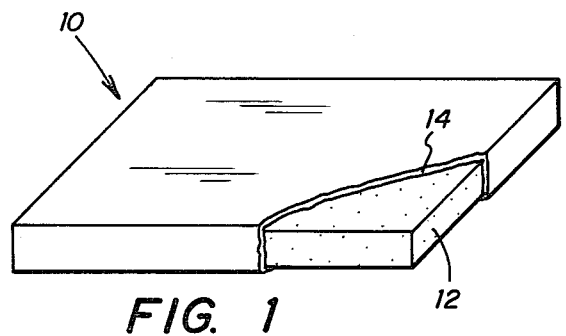
FIG. 1 is a front elevational cut away view of a cushion structure embodying the invention.

The present invention may be used in the manufacture of a variety of preformed lightweight stable gel structures. One embodiment of the present invention is illustrated, as a cushion 10 in FIG. 1. Although the cushion structure 10 is shown as being substantially rectangular, it may be of any desired shape.

Figure 2:
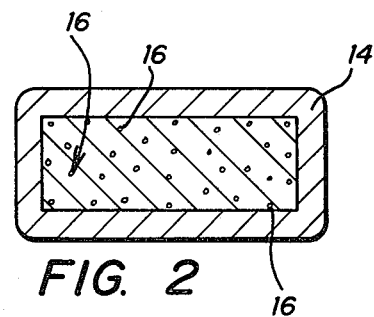
FIG. 2 is an enlarged, cross sectional view of the cushion illustrated in FIG. 1 which illustrates the dispersion of glass microspheres throughout and a covering.

Cushion structure 10 is constructed from a lightweight gel core 12 molded to the desired shape, and covered by a wall cover 14. Wall cover 14 may comprise any suitable material, preferably elastic, such as latex rubber or a porous elastic fabric. FIG. 2 is a side cross-sectional view of the cushion structure 10 in FIG. 1. FIG. 2 illustrates the lightweight gel core 12 with a multiplicity of glass microspheres 16 dispersed throughout. The lightweight gel core 12 is covered by wall means 14, which may be constructed of multiply layers as disclosed in U.S. Pat. No. 3,308,491.

The lightweight gel core 12 is preferably formed with a dielectric silicon gel of the type manufactured and sold by Dow Chemical Company of Midland, Mich., General Electric Company of Schenectady, N.Y. and others. The silicon gel preferably is a reaction product of the reaction of methyl polysiloxane containing silicon-bonded vinyl groups and a methyl polysiloxane containing SiH groups in which the reaction is catalyzed by platinum. The reaction mixture is preferably an intimate mixture consisting of (1) an organosiloxane having a viscosity of from 100 to 10,000 cs. at 25° C. and being a copolymer consisting essentially of units of the formula $RViSiO$, $R_2SiO$, and $CH_3R_2SiO_5$ where each R individually is selected from the group consisting of methyl and phenyl radicals and the Vi represents a vinyl radical, at least 0.174 molar percent of the units in said copolymer and being the said RViSiO units (this mixture is hereinafter referred to as Mixture I) and (2) a liquid hydrogenosiloxane of the average general formula

where each R is as above defined and "n" has an average value such that the viscosity of the hydrogenosiloxane is no more than 10,000 cs. at 25° C. (hereinafter referred to as Mixture II), no more than 25 molar percent of the total R radicals present in Mixture I and Mixture II being phenyl, (3) a platinum catalyst in an amount sufficient to furnish at least 0.1 part per million of Pt based on the combined weight of Mixture (I) and Mixture (II), and (4) the inert hollow, inorganic microspheres.

The inert, hollow, inorganic microspheres are hollow spheres typically in the range of from about 20 to about 200 microns in diameter. Such microspheres are commonly made from glass. In general, microspheres have a diameter less than 0.5 millimeters. When the diameter of the spheres is greater than 0.5 millimeters, they are commonly referred to as macrospheres. Macrospheres typically range in size from 0.5 to 11 millimeters and may be made from the smaller microspheres. The size of the inert, hollow, inorganic spheres utilized in the present invention is not critical as long as the stable gel formed retains the desired strength, resiliency and memory characteristics. Thus, one skilled in the art will appreciate that macrospheres may be desirable for use in larger structures. As used herein "glass microspheres" shall mean inert, hollow, inorganic microspheres or macrospheres. Preferably, the glass microspheres are less than about 200 microns in diameter such as those sold by the 3M Company, St. Paul, Minn., under the trademark "3M" Brand Glass Bubbles".

The reaction mixture is composed of a gel mixture to which glass microbubbles have been added in the desired concentration. As used herein, "gel mixture" refers to the combination of Mixture I, Mixture II and catalyst. The concentrations of the component chemicals in the gel mixture may be varied according to the characteristics sought in the resulting product. Preferably, the gel mixture is comprised of catalyst in the concentration described above, 50 to 60% of Mixture I and the remaining portion being Mixture II. This gel mixture permits the formation of lightweight gel core which is self-contained and is resilient. As used herein "lightweight gel" means a composition formed by the reaction of the reaction mixture to produce a silicon gel with glass microspheres dispersed throughout.

The gel mixture is mixed and stored at low temperature to inhibit reaction. The mixing temperature may vary according to the degree of inhibition desired. Refrigerating the gel mixture at approximately 15° F. has been found sufficient to essentially prevent any reaction of the gel mixture.

The reaction mixture is formed by preparing the gel mixture and admixing glass microspheres therewith. Preferably, the concentration of glass microspheres is from 1 to about 30% of the total reaction mixture weight. When the concentration of glass microspheres exceeds 30% the strength of the gel core formed and its elasticity decreases rapidly. Gel cores formed with higher concentrations of glass microspheres easily tear, and when deformed under pressure are slow to return to shape after the pressure has been removed.

The glass microspheres are thoroughly admixed with the gel mixture while the gel mixture is maintained at low temperature to inhibit reaction. The thoroughly mixed reaction mixture thus formed is poured into a mold of desired shape where the temperature is elevated to initiate reaction of the gel mixture thereby forming a lightweight gel core from the reaction mixture.

A larger percentage of glass microspheres may be utilized where the resulting gel is contained within an elastic envelope which when combined with the gel would provide the desired elasticity, resiliency and strength. The concentration of glass microspheres may be varied to achieve the desired product characteristics according to several interrelated functions such as the desired weight reduction, desired elasticity, desired gel strength, desired resiliency and type of covering. Increasing the amount of glass microspheres reduces weight, resiliency and gel strength. Those skilled in the art will appreciate that the characteristics of the total structure vary according to both the gel composition and the type of covering.

The reaction or the gel mixture will proceed at room temperature; however, it is preferable to elevate the temperature to speed the reaction. It is also preferable to preheat the molds to approximately 220° F. Preheating the mold and elevating the temperature speeds the reaction and also tends to maintain the dispersion of the glass microspheres uniformly throughout the gel during reaction. The temperature is preferably maintained during reaction from about 200° F. to about 240° F. The glass microspheres are thus substantially uniformly distributed throughout the resulting lightweight gel. In addition, the increased reaction rate permits the rate of production to be increased.

In the refrigerated reaction mixture, the glass bubbles tend to migrate to the surface of the reaction mixture when agitation is removed. Thus, the reaction mixture containing the glass microspheres is preferably stirred or agitated before pouring the reaction mixture into the mold. Preheating the mold permits the temperature of the reaction mixture to be raised rapidly and speed the reaction which prevents the migration of the glass microspheres to the surface of the reaction mixture in the mold.

The time for complete reaction varies depending on a number of factors, such as, the composition of the gel mixture, the temperature, the size and shape of the item to be molded, and the concentration of glass microspheres. The reaction time generally decreases as the concentration of glass microspheres increases.

The lightweight gel core formed by reaction of the reaction mixture is sticky and is preferably covered with a suitable covering. Once the lightweight gel core is formed the stickiness of its surface may be reduced to facilitate handling by thoroughly coating the lightweight gel core with a talcum or other suitable powder to eliminate the sticky character of the surface. Preferably a suitable covering is placed over the lightweight gel core to permit ease of handling and cleaning of the final product.

The covering applied is preferably a yieldable covering which does not substantially constrain the deformation of lightweight gel core when pressure is applied. The covering may be porous or impermeable as desired. Such a covering may be attached to the lightweight gel core by an adhesive or by impregnating the cover or portion thereof into the reaction mixture before the reaction is completed. Multiple layers of coverings may be used if desired. These additional layers may be employed to provide a removal cover. Alternatively, additional covering layers may be attached to the lightweight gel core by any suitable means, for example, sewing to a covering fabric which has been impregnated into the lightweight gel core.

Figure 3:
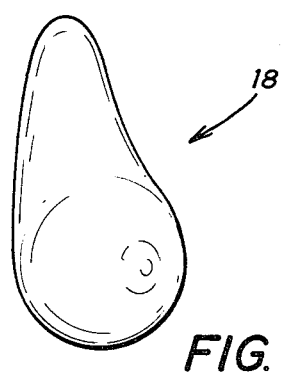
FIG. 3 is a perspective view of the artificial breast prothesis embodying the present invention.
Figure 4:
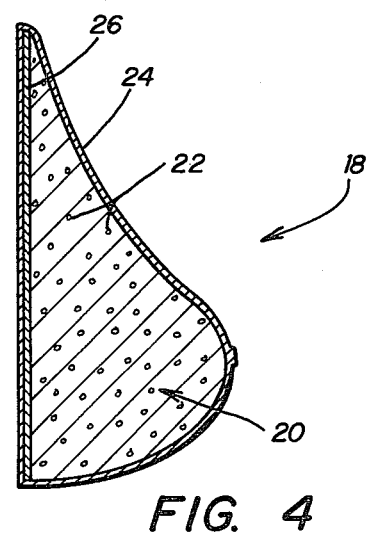
FIG. 4 is a vertical cross-sectional view of the breast prothesis of FIG. 1 which reveals the dispersion of glass microspheres and the breast form cover.

FIG. 3 illustrates another embodiment of the present invention as an external breast prosthesis 18. Such an external breast prosthesis 18 is formed as described above and molded to simulate the human breast. FIG. 4 is a vertical cross-sectional view of external breast prosthesis 18. Prosthesis 18 is comprised of lightweight gel core 20 with a multiplicity of glass microspheres 22 dispersed throughout. The prosthesis 18 is completed by the addition of covering layer 24 of elastic material which is attached to back piece 26. Back piece 26 may be attached to lightweight gel core 16 by impregnating back piece 26 into the reaction mixture before the reaction was completed as disclosed and described in U.S. Pat. No. 4,019,209.

Figure 5:
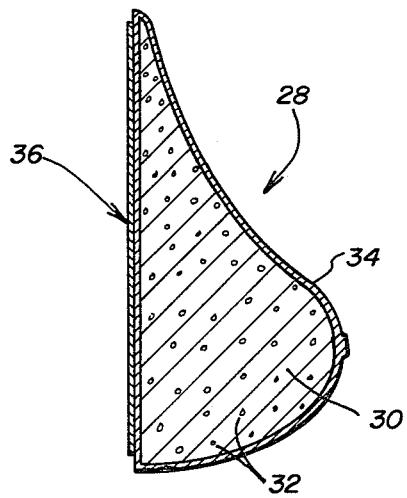
FIG. 5 is a side cross-sectional view of a breast prothesis to be surgically implanted.

Yet another embodiment of the present invention is illustrated in FIG. 5. FIG. 5 shows a vertical cross-sectional view of an implantable breast prosthesis 28 suitable for surgical implantation in the human body. Implantable breast prosthesis 28 is constructed of a lightweight gel core 30 containing glass microspheres 32 and molded in accordance with the method of the present invention. The prosthesis 28 covered with a covering material 34 compatible with human tissue such as polyester or polyamide fabrics. Means for securing the implantable prosthesis 28 to the body is provided by a felt-like layer 36 to provide an area for tissue ingrowth as disclosed and described in U.S. Pat. No. 3,665,520.

EXAMPLE

The following example is presented in order to better facilitate the understanding of the subject invention and its benefits, but is not intended to limit the scope thereof.

A breast prosthesis was molded from the reaction mixture of the present invention. First, a gel mixture was prepared by admixing the catalyst with Mixture I and Mixture II at 15° F. The concentration of Mixture I was about 60% of total gel mixture weight. The concentration of Mixture II was about 40% of the total gel mixture weight, and the remaining portion was the trace amount of catalyst. The reaction mixture was prepared by admixing glass microspheres in a concentration of 30% of total reaction mixture weight with the gel mixture while maintaining the temperature at 15° F.

The reaction mixture was stirred to disperse the glass microspheres and poured into a preheated mold of breast size and shape. The mold was preheated to approximately 220° F. and the temperature was maintained in the range of 200° F. and 230° F. during reaction.

Breast prothesis formed in this manner required approximately 30 to 45 minutes to react completely. The same reaction at room temperature required approximately 18 to 20 hours to complete. Breast prothesis manufactured completely from the gel mixture without glass microspheres required approximately twice as long as to react completely than breast prothesis of similar size formed in accordance with the present invention of similar size. In addition, breast prosthesis made completely from the gel mixture weigh approximately 33% more than forms which incorporate 30% glass microspheres. Thus, the present invention permits the more economical manufacture of stable gel forms by replacing costly gel with less expensive glass microspheres and by increasing the production rate. Additionally, the structures formed from the present invention are lighter and less expensive to ship.

Breast prothesis made in accordance with U.S. Pat. No. 4,019,209 have been very successful, but have been considered too heavy by many users. Breast prothesis manufactured in accordance with the present invention are significantly lighter and less fatiguing to wear while maintaining the desirable characteristics of the earlier prothesis.

Having described the invention in connection with certain embodiments thereof, it is to be understood that certain modifications may now suggest themselves to those skilled in the art and it is intended to cover such modifications as fall within the scope of the appended claims.

I claim:
1. The method of forming a lightweight stable gel comprising the steps of:
    (a) preparing at low temperature a gel mixture by admixing;
        (i) methyl polysiloxane containing silicon-bonded vinyl groups, with
        (ii) methyl polysiloxane containing SiH groups, and
        (iii) a platinum catalyst;
    (b) mixing glass microspheres into said gel mixture;
    (c) pouring the resulting mixture into a mold of desired shape; and
    (d) allowing the resulting mixture to react until a stable silicon gel structure is formed.
2. The method of claim 1 wherein said low temperature is a temperature at which the reaction of said gel mixture is substantially inhibited.
3. The method of claim 1 wherein said mold is preheated.
4. The method of claim 1 wherein the reaction of said resulting mixture is preformed at a temperature from about 200° F. to about 240° F.
5. The product formed by the method of claims 1, 2, 3 or 4.
6. The method of claims 1, 2, 3 or 4 wherein said glass microspheres are hollow, inorganic spheres with a diameter less than about 200 microns.
7. The method of forming a lightweight stable gel comprising the steps of:
    (a) preparing at low temperature a gel mixture containing from about 50 to 60 weight percent of a methyl polysiloxane containing silicon-bonded vinyl groups, and from about 50 to 40 weight percent methyl polysiloxane containing SiH groups and a platinum catalyst;
    (b) mixing from 1 to about 30 weight percent glass microspheres into said gel mixture;
    (c) pouring the resulting mixture into a mold of a desired shape; and
    (d) allowing the resulting mixture to react until a stable silicon gel structure is formed.
8. The method of claim 7 wherein said low temperature is a temperature at which the reaction of said reaction mixture is substantially inhibited.
9. The method of claim 7 wherein said mold is preheated at a temperature in the range of about 200° to about 240° F.
10. The method of claim 8 wherein the reaction of said resulting mixture is preformed at a temperature of about 200° F. to about 240° F.
11. The product formed by the method of claim 7, 8, 9 or 10.
12. The method of claims 7, 8, 9 or 10 wherein said glass microspheres are hollow inorganic spheres of a diameter less than about 200 microns.
13. The product formed by the method of claim 12.
14. The method of claim 7 which further comprises the steps of agitating the resulting mixture while at low temperature to disperse said glass microspheres after the step of mixing of said glass microspheres with said gel mixture and before the step of pouring the resulting mixture into a mold.

15. The method of forming a lightweight stable gel which comprises the steps of claim 7 and further comprises the step of:
covering said stable silicon gel structure with a flexible wall means.

16. The method of claim 15 wherein said wall means is impermeable.

17. The method of claim 15 wherein said wall means is porous.

18. The method of forming a lightweight stable gel structure which comprises the steps of the method of claim 7 and further comprises the steps of:
impregnating a fabric panel in said resulting mixture after it has been poured into the mold but before the reaction is completed.

19. The method of claim 18 and which further comprises the steps of:
(a) coating said stable silicon gel structure with a powder to render the surface non-tacky; and
(b) applying over all surfaces of said structure a cover.

20. The method of claim 19 in which said cover or portion thereof is of elastic material.

21. The method of claim 19 in which said cover is impermeable.

22. A lightweight stable gel structure comprising:
(a) a preformed self-contained stabilized gel structure of desired size and shape; and
(b) said gel structure containing a multiplicity of glass microspheres dispersed throughout said gel structure wherein said gel is a silicon gel, the reaction product of a methyl polysiloxane containing silicon-bonded vinyl groups and methyl polysiloxane containing SiH groups which have been catalyzed by platinum to establish and substantially retain said shape.

23. A lightweight stable gel structure comprising:
(a) a preformed self-contained stabilized gel structure of desired size and shape;
(b) said gel structure containing a multiplicity of glass microspheres dispersed throughout said gel structure; and
(c) an elastic fabric cover which yields in response to pressures exerted thereon by said gel in which said gel is a silicon gel, the reaction product of a methyl polysiloxane containing silicon-bonded vinyl groups and methyl polysiloxane containing SiH groups which have been catalyzed by platinum to establish and substantially retain said shape.

24. A combination set forth in claims 22, or 26, in which said microspheres are hollow, inorganic spheres having a diameter of less than about 200 microns.

25. The combination set forth in claim 23 in which said glass microspheres are present in a concentration of from 1 to about 30% by weight of the total gel structure weight.

26. The combination set forth in claim 25 wherein said glass microspheres are hollow, inorganic spheres of a diameter less than about 200 microns.

27. The combination set forth in claim 23 in which said gel structure is a dielectric silicon gel with glass microspheres dispersed throughout catalyzed to stably retain substantially said shape and coated with powder to avoid sticking to said cover.

28. The combination set forth in claim 23 in which a layer of elastic fabric is impregnated within said gel.

29. The combination set forth in claim 28 in which said elastic fabric cover is secured to said impregnated layer.

30. The combination set forth in claim 23 in which said structure is powder coated to prevent sticking to said cover.

31. The combination set forth in claim 28 in which said structure is in the form of a breast or portion thereof suitable for use by a mastectomy patient.

32. The combination set forth in claim 23 in which said structure is in the form of a cushion.

33. The combination set forth in claim 26 in which said structure is in the form of a breast or portion thereof suitable for use by a mastectomy patient.

34. The combination set forth in claim 26 in which said structure is in the form of a cushion.

35. The composition of matter comprising:
(a) a stabilized silicon gel which is the reaction product of a methyl polysiloxane containing silicon-bonded vinyl groups and methyl polysiloxane containing SiH groups which have been catalyzed by platinum to establish and substantially retain a predetermined shape; and
(b) said stabilized silicon gel containing a multiplicity of glass microspheres dispersed throughout said stabilized silicon gel.

* * * * *

UNITED STATES PATENT AND TRADEMARK OFFICE
CERTIFICATE OF CORRECTION

PATENT NO. : 4,380,569
DATED : April 19, 1983
INVENTOR(S) : Robert E. Shaw

It is certified that error appears in the above—identified patent and that said Letters Patent is hereby corrected as shown below:

Column 1, line 52 delete "of".
Column 7, line 14 delete "steps" and insert --step-- therefor.

Signed and Sealed this

Ninth Day of August 1983

[SEAL]

Attest:

GERALD J. MOSSINGHOFF

Attesting Officer

Commissioner of Patents and Trademarks